United States Patent [19]

Golik

[11] Patent Number: 4,921,700

[45] Date of Patent: May 1, 1990

[54] BBM-1675C AND D ANTITUMOR ANTIBIOTICS

[75] Inventor: Jerzy Golik, Syracuse, N.Y.

[73] Assignee: Bristol-Myers Company, New York, N.Y.

[21] Appl. No.: 55,209

[22] Filed: May 28, 1987

Related U.S. Application Data

[62] Division of Ser. No. 770,335, Aug. 27, 1985, abandoned.

[51] Int. Cl.$^5$ .......................... A61K 35/74; C12P 1/04
[52] U.S. Cl. ...................................... 424/117; 435/169
[58] Field of Search .......................... 424/117; 435/169

[56] References Cited

U.S. PATENT DOCUMENTS

| | | | |
|---|---|---|---|
| 4,594,248 | 6/1986 | Wilton et al. | 424/117 |
| 4,661,353 | 4/1987 | Wilton et al. | 424/117 |
| 4,675,187 | 6/1987 | Konishi et al. | 424/117 |

Primary Examiner—Ronald W. Griffin
Attorney, Agent, or Firm—Aldo A. Algieri

[57] ABSTRACT

There is provided new antitumor antibiotic substances designated herein as BBM-1675C and BBM-1675D, said substances being produced by selective chemical hydrolysis of the bioactive components BBM-1675A$_1$ (esperamicin A$_1$) or BBM-1675A$_2$ (esperamicin A$_2$). The new antitumor antibiotics exhibit both antimicrobial activity and antitumor activity.

4 Claims, 13 Drawing Sheets

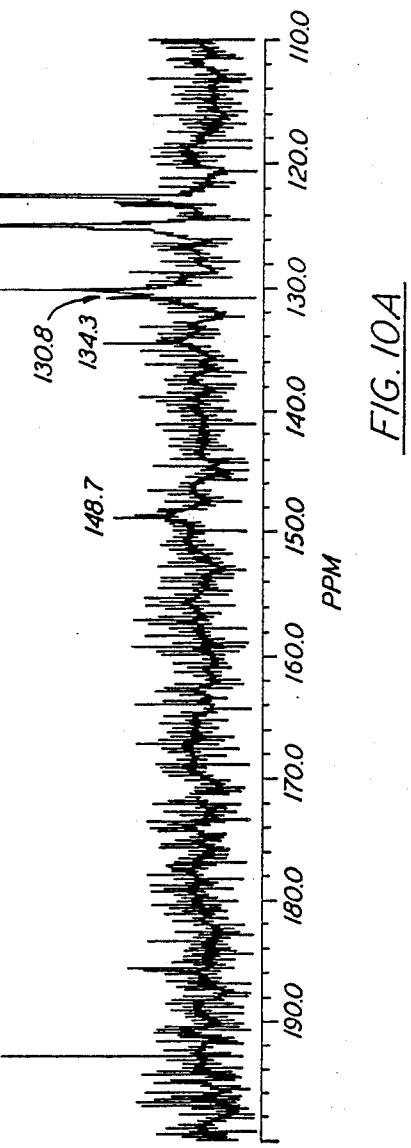

BBM-1675C AND D ANTITUMOR ANTIBIOTICS

CROSS-REFERENCE TO RELATED APPLICATION

This application is a divisional of our prior, co-pending application Ser. No. 770,335, filed Aug. 27, 1985, now abandoned.

BACKGROUND OF THE INVENTION

1. Field of the Invention

This invention relates to new antitumor antibiotic substances and to their production and isolation. 2. Disclosure Statement The antitumor compounds of the present invention have not yet been identified in terms of structure. In view of their unique physical, chemical and biological properties, however, applicant believes that the BBM-1675C and BBM-1675D antibiotics are novel substances.

United Kingdom Patent Application No. 2,141,425, published Dec. 19, 1984, discloses fermentation of *Actinomadura verrucosospora* strain H964-92 (ATCC 39334) or *Actinomadura verrucosospora* strain A1327Y (ATCC 39638) to produce a new antitumor antibiotic complex designated as BBM-1675. Two major bioactive components of the BBM-1675 complex described therein were designated as BBM-1675$A_1$ and BBM-1675$A_2$. The structures of the BBM-1675$A_1$ and BBM-1675$A_2$ antibiotics, also known as esperamicin $A_1$ and esperamicin $A_2$, respectively, have not yet been elucidated, but both components exhibit excellent antimicrobial and antitumor activity.

U.S. Pat. No. 4,530,835, issued July 23, 1985 to Bunge et al., discloses fermentation of an unidentified Actinomycete isolate WP-444 (ATCC 39363) to produce antitumor antibiotics designated CL-1577A and CL-1577B. The structures of the CL-1577 antibiotics have not yet been elucidated, but the characterizing properties given for the antibiotics indicate that CL-1577A and CL-1577B are similar in structure to the BBM-1675 antibiotics, and especially BBM-1675$A_1$ and $A_2$ mentioned above in United Kingdom Patent Application No. 2,141,425.

There is disclosed by R. H. Bunge et al., in *J. Antibiotics*, 37(12), 1566-1571 (1984) the fermentation of *Actinomadura sp.* (ATCC 39363) to produce a bioactive complex from which two major components, PD 114,759 and PD 115,028, were isolated. In J. Chem. Soc. Chem. Commun., 919-920 (1985), J. H. Wilton et al. described the partial structural elucidation of the antibiotics PD 114,759 and PD 115,028. The production, isolation and characterization of the PD 114,759 and PD 115,028 antibiotics appear to be identical to the above-mentioned CL-1577A and CL-1577B antibiotics, respectively.

European Patent Application No. 95,154, published Nov. 30, 1983, discloses fermentation of *Actinomadura pulveraceus sp. nov.* No. 6049 (ATCC 39100) to produce antitumor antibiotics designated WS 6049-A and WS 6049-B. The structures of the WS 6049 antibiotics have not yet been elucidated, but the characterizing properties given for the antibiotics indicate that WS 6049-A and WS 6049-B are related in structure to the BBM-1675 antibiotics of United Kingdom Patent Application No. 2,141,425 and to the CL-1577 antibiotics of U.S. Pat. No. 4,530,835. Spectral data show, however, that neither WS 6049-A nor WS 6049-B is identical to any of the BBM-1675 components. Moreover, the producing organism described in European Patent Application No. 95,154 may be clearly differentiated from *Actinomadura verrucosospora* employed in United Kingdom Patent Application No. 2,141,425 in the color of its aerial mycelium on ISP Medium Nos. 2, 3 and 4, in its positive milk peptonization and in its positive utilization of D-fructose, D-mannitol, trehalose and cellulose.

SUMMARY OF THE INVENTION

There is provided by the present invention new antitumor antibiotic substances designated herein as BBM-1675C and BBM-1675D, also known as BMY-27305 and BMY-27307, respectively, said substances being produced by selective chemical hydrolysis of the bioactive components BBM-1675$A_1$ (esperamicin $A_1$) or BBM-1675$A_2$ (esperamicin $A_2$), which are themselves produced by cultivating a BBM-1675-producing strain of *Actinomadura verrucosospora*. The bioactive substances BBM-1675C and BBM-1675D may be separated and purified by conventional chromatographic procedures, and both substances exhibit excellent antimicrobial and antitumor activity.

DESCRIPTION OF THE DRAWINGS

FIG. 10A shows the $^{13}C$ magnetic resonance spectrum (110-200 ppm) of BBM-1675D in $CDCl_3$+10% CD30D (90.6 MHz).

DESCRIPTION OF THE INVENTION

Figure 1:
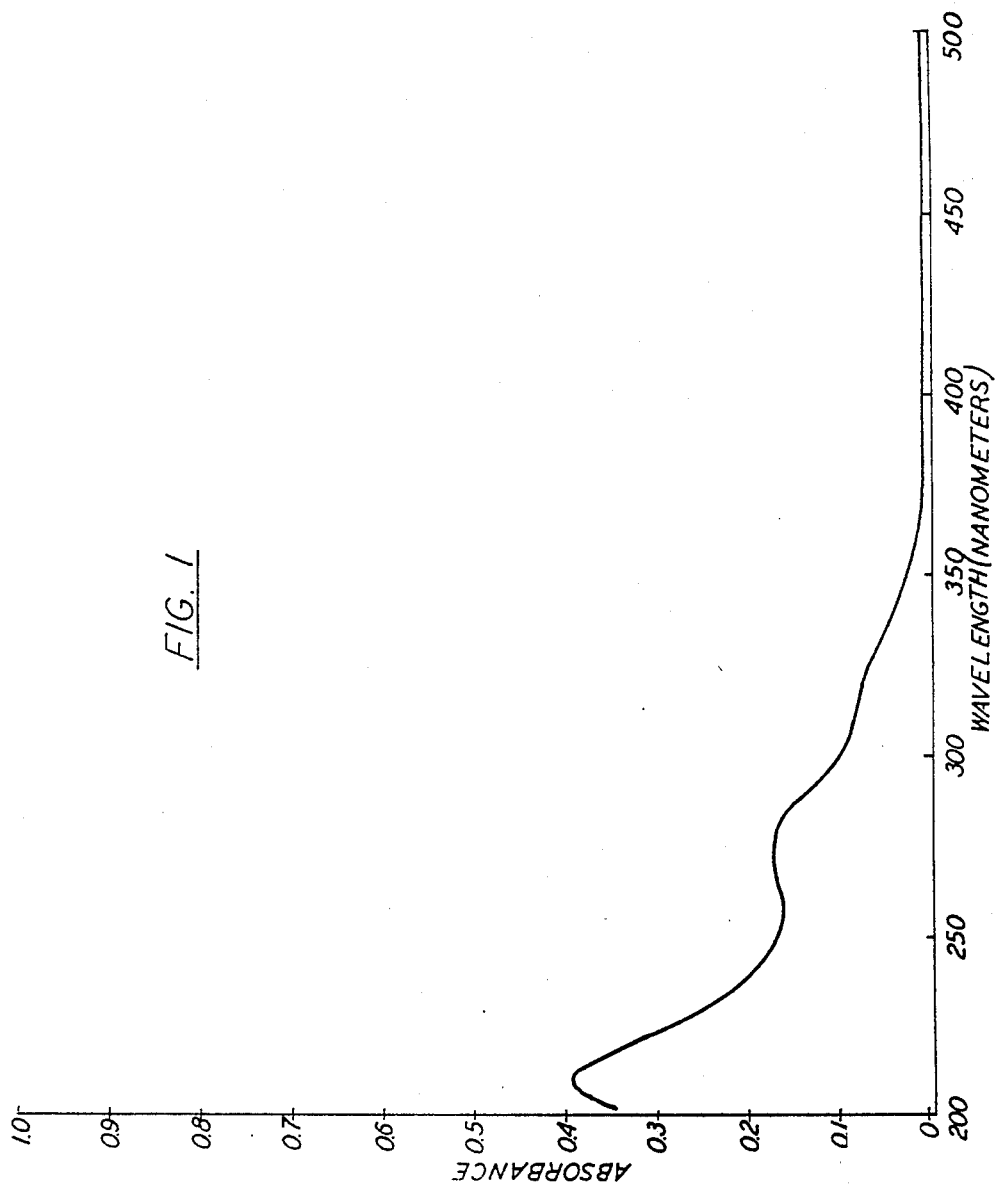
FIG. 1 shows the ultraviolet absorption spectrum of BBM-1675C.

This invention relates to two novel antitumor antibiotic substances designated herein as BBM-1675C and BBM-1675D, also known as BMY-27305 and BMY-27307, respectively, said substances being produced by selective chemical hydrolysis of the bioactive components BBM-1675$A_1$ (esperamicin $A_1$) or BBM-1675$A_2$ (esperamicin $A_2$), which are themselves produced by cultivating a BBM-1675-producing strain of *Actinomadura verrucosospora*, most preferably *Actinomadura verrucosospora* strain H964-92 (ATCC 39334) or *Actinomadura verrucosospora* strain A1327Y (ATCC 39638), or a mutant thereof. In another aspect, the present invention provides a process for producing the BBM-1675C substance by selective hydrolysis of the bioactive components BBM-1675A₁ or BBM-1675A₂ In a further aspect, the present invention provides a process for the preparation of BBM-1675D by selective hydrolysis of the BBM-1675C substance or, more preferably, from the bioactive components BBM-1675A₁ or BBM-1675A₂. The isolation and purification of BBM-1675C and BBM-1675D from the reaction mixture may be accomplished by conventional chromatographic procedures.

The bioactive substances BBM-1675C and BBM-1675D exhibit antimicrobial activity against a broad spectrum of microorganisms and have also been shown to exhibit inhibitory activity against various mouse tumor systems, such as P-388 leukemia and B16 melanoma. The newly described substances of the present invention, therefore, may be used as antimicrobial agents or as antitumor agents for inhibiting mammalian tumors.

During the course of degradation studies to elucidate the structure of the antitumor antibiotics BBM-1675A₁ (esperamicin A₁) and BBM-1675A₂ (esperamicin A₂), a mixture of components were produced which lead to the isolation and identification of two inactive fragments, compounds of the Formulas 1 and 2, respectively. However, it was surprisingly found that the chemical degradation lead to the stepwise liberation of two bioactive fragments BBM-1675C and BBM-1675D. Even more surprising, it was found that the two different antibiotics BBM-1675A₁ and A₂ produced the same bioactive fragments as illustrated in Scheme 1. Still more surprising, the smaller molecular weight fragments BBM-1675C and D (having approximately 70% and 55% of the molecular weight of the parent antibiotics BBM-1675A₁ and A₂, respectively) were found to be more effective than BBM-1675A₂ and comparable to BBM-1675A₁ as antitumor and antimicrobial agents.

SCHEME 1

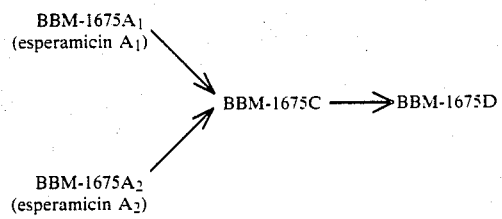

The BBM-1675C and BBM-1675D substances may be prepared by selective chemical hydrolysis of the antibiotic BBM-1675A₁ as outlined in Scheme 2.

SCHEME 2

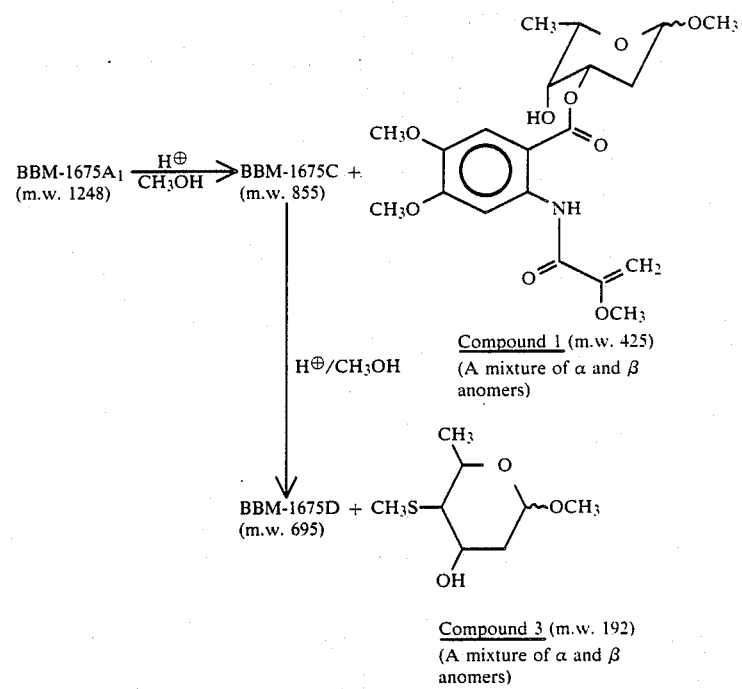

The starting BBM-1675A₁ compound is prepared according to the procedure described in United Kingdom Patent Application No. 2,141,425, published Dec. 19, 1984. The purified BBM-1675A₁ component is hydrolyzed with a mineral or organic acid such as hydrogen chloride, sulfuric acid, p-toluenesulfonic acid, benzenesulfonic acid or the like, in an organic or mixed aqueous-organic inert solvent at a temperature of about 0° C. to the refluxing temperature of the solvent until a substantial amount of the desired BBM-1675C or BBM-1675D is produced. Preferably, the hydrolysis is carried out in $C_1$–$C_6$ alcohol solvents, and most preferably, the alcoholysis is carried out in methanol. The temperature of the reaction is not critical, but it is preferred to conduct the reaction at about ambient temperature to 60° C., and most preferably from about 40° to 60° C.

The selective hydrolysis of BBM-1675A₁ proceeds in a stepwise manner with the initial production of the BBM-1675C antibiotic and the inactive fragment of Formula 1. Subsequent or continued treatment under hydrolyzing conditions leads to the liberation of a mixture of α and β anomers of the thiosugar of Formula 3 and the production of the antibiotic BBM-1675D. It should be appreciated by those skilled in the art that altering the reaction conditions such as time, temperature and concentration of acid will produce varying relative amounts of the antibiotics BBM-1675C and D. Thus, it is desirable to monitor the progress of reaction by thin layer chromatography as described in the examples herein.

When it is desired to prepare only the BBM-1675D antibiotic, the selective hydrolysis is preferably carried out with an organic acid such as p-toluenesulfonic acid as described herein to yield a quantitative amount of BBM-1675D.

The BBM-1675C and BBM-1675D substances may also be prepared by selective chemical hydrolysis of the antibiotic BBM-1675A$_2$ as outlined in Scheme 3.

The discovery, as described herein, that the same BBM-1675C and D antibiotics are produced from two different antibiotics BBM-1675A$_1$ and BBM-1675A$_2$ with the concurrent loss of two inactive fragments of Formulas 1 and 2, respectively, and the thiosugar of Formula 3, provides an additional advantage for the present invention. Accordingly, in a further aspect of the present invention, there is provided a process for the selective hydrolysis of a mixture of BBM-1675A$_1$ and A$_2$ to produce BBM-1675C and D as illustrated in Scheme 4.

SCHEME 4

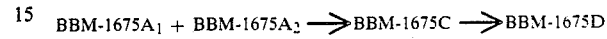

BBM-1675A$_1$ + BBM-1675A$_2$ $\longrightarrow$ BBM-1675C $\longrightarrow$ BBM-1675D

SCHEME 3

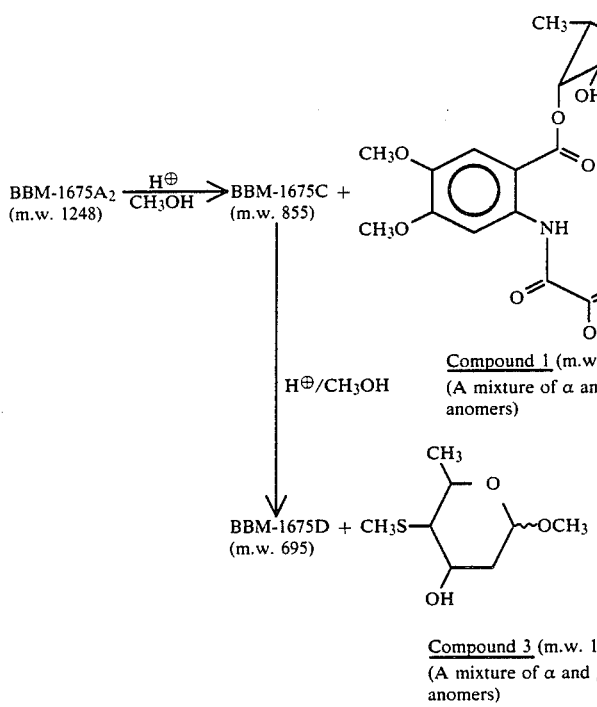

The starting BBM-1675A$_2$ compound is prepared according to the procedure described in United Kingdom Patent Application No. 2,141,425, published Dec. 19, 1984. The selective hydrolysis of purified BBM-1675A$_2$ likewise proceeds in a stepwise manner with the initial production of the BBM-1675C antibiotic and the inactive fragment of Formula 2. Continued treatment under hydrolyzing conditions leads to the liberation of a mixture of α and β anomers of the thiosugar of Formula 3 and the production of the antibiotic BBM-1675D.

The reaction conditions utilized for the selective chemical hydrolysis of BBM-1675A$_2$ are substantially the same as those utilized for the hydrolysis of BBM-1675A$_1$ described above. In a manner similar to the production of BBM-1675D from BBM-1675A$_1$, when it is preferred to produce only the BBM-1675D antibiotic, the hydrolysis of BBM-1675A$_2$ is carried out until substantially all of BBM-1675A$_2$ and BBM-1675C is converted to BBM-1675D. Most preferably, the hydrolysis is carried out with an organic acid such as p-toluenesulfonic acid.

This advantage becomes apparent when one considers that the relative amounts of BBM-1675A$_1$ and A$_2$ produced in the fermentation process is subject to variability. The production of BBM-1675C and D is therefore independent of the relative amounts of BBM-1675A$_1$ and A$_2$ utilized as starting material in the present invention.

Figure 11A:
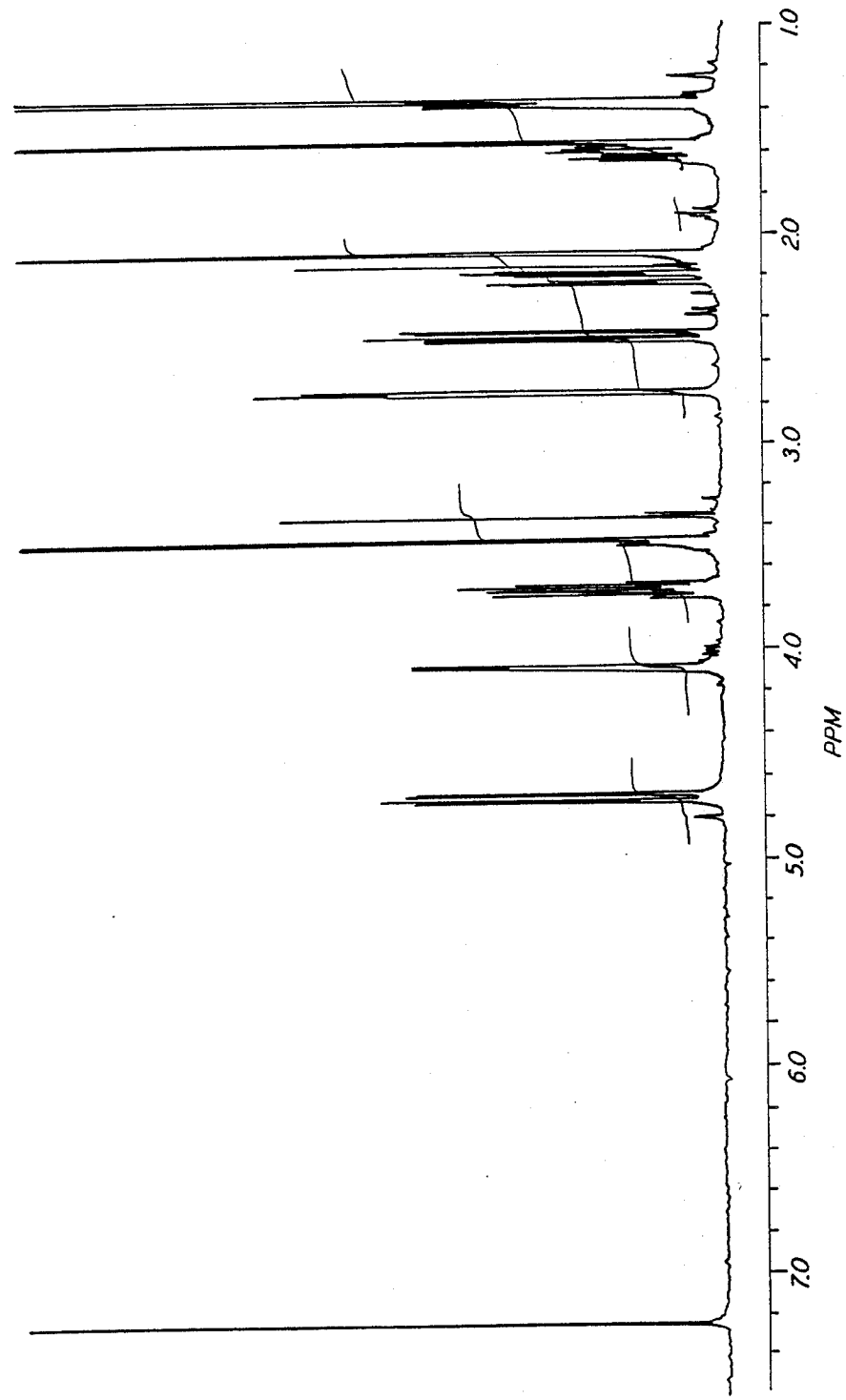
FIG. 11A shows the proton magnetic resonance spectrum of compound 3A ($\alpha$-anomer) in $CDCl_3$ (360 MHz).
Figure 11B:
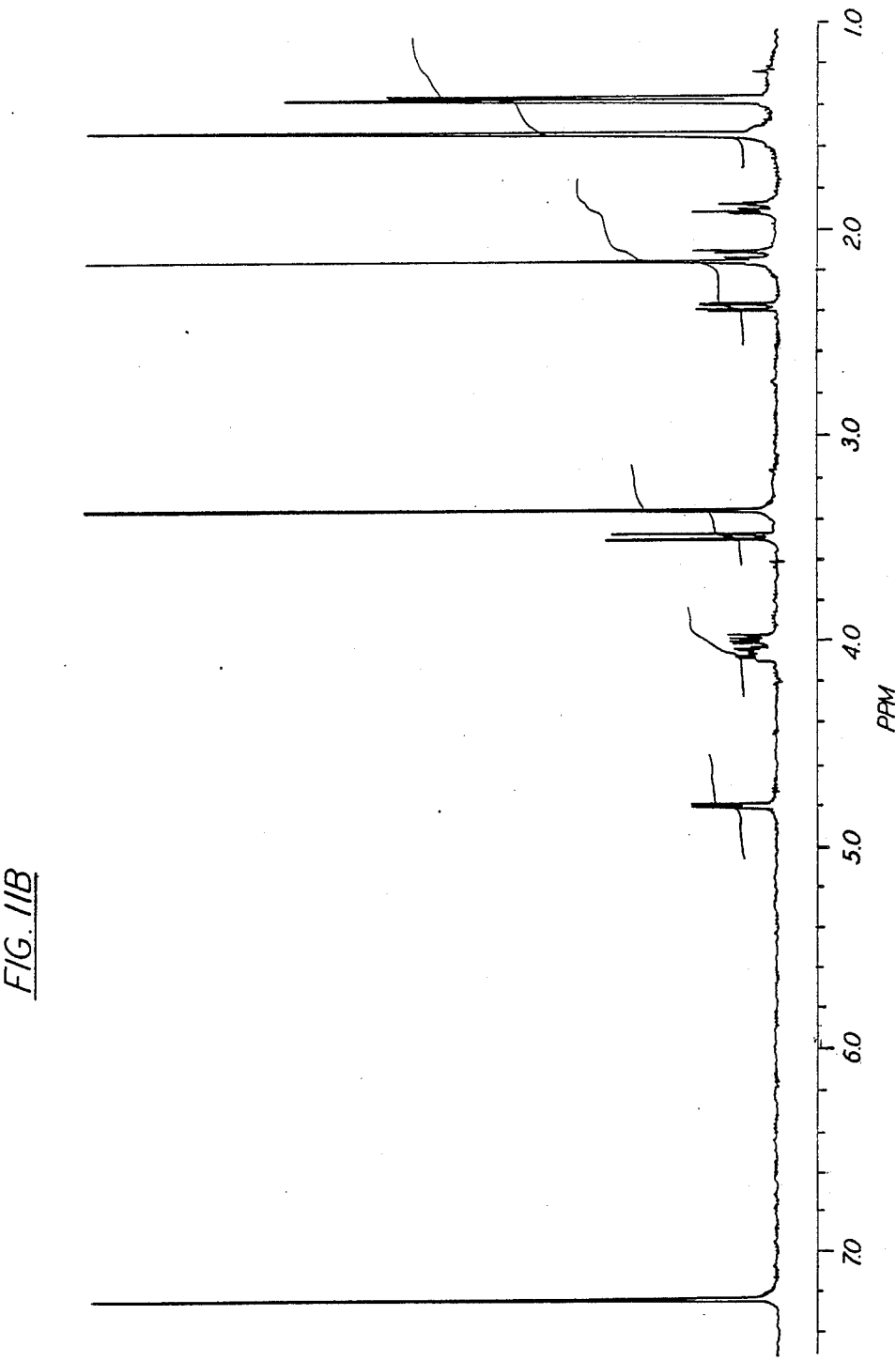
FIG. 11B shows the proton magnetic resonance spectrum of compound 3B ($\beta$-anomer) in $CDCl_3$ (360 MHz).

As described herein, the hydrolysis of the BBM-1675A$_1$, A$_2$ and C antibiotics results in the release of an inactive thiosugar fragment. The said thiosugar was isolated to provide further information into the chemical structure of the BBM-1675C antibiotic and hence, for the BBM-1675A$_1$ and A$_2$ antibiotics. The compound of Formula 3 was identified as a mixture of α and β anomers of a thiosugar which has the structure illustrated in Schemes 2 and 3. Further characterization was made possible when the products of the alcoholysis, the α and β anomers, were separated. The proton magnetic resonance spectra (360 MHz) of the compound 3A (α-anomer) and compound 3B (β-anomer) are shown in FIGS. 11A and 11B, respectively. From an analysis of the spectral data, the thiosugar methyl glycosides of Formula 3 were tentatively assigned the relative stereochemistry of the formula

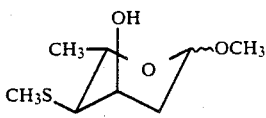

At the present time, the absolute stereochemistry, i.e. D or L, has not yet been determined. Accordingly, based on the present interpretation of the spectral data, it is concluded that the thiosugar of Formula 3 (less the $CH_3$ group from the anomeric methoxy which is incorporated during the methanolysis) is a component in the structure of the antibiotic BBM-1675C and furthermore, is a component in the structure of the starting BBM-1675$A_1$ and $A_2$ antibiotics.

PHYSICO-CHEMICAL PROPERTIES OF BBM-1675C

Description: amorphous solid
Ultraviolet absorption spectrum: See FIG. 1
Instrument: Hewlett-Packard 8458
Solvent: methanol
Concentration: 0.0155 g/l

| $\lambda_{max}$ (nm) | absorptivities |
| --- | --- |
| 210 | 21,770 |
| 274 | 9,340 |
| 313 sh (shoulder) | 4,190 |

Figure 3:
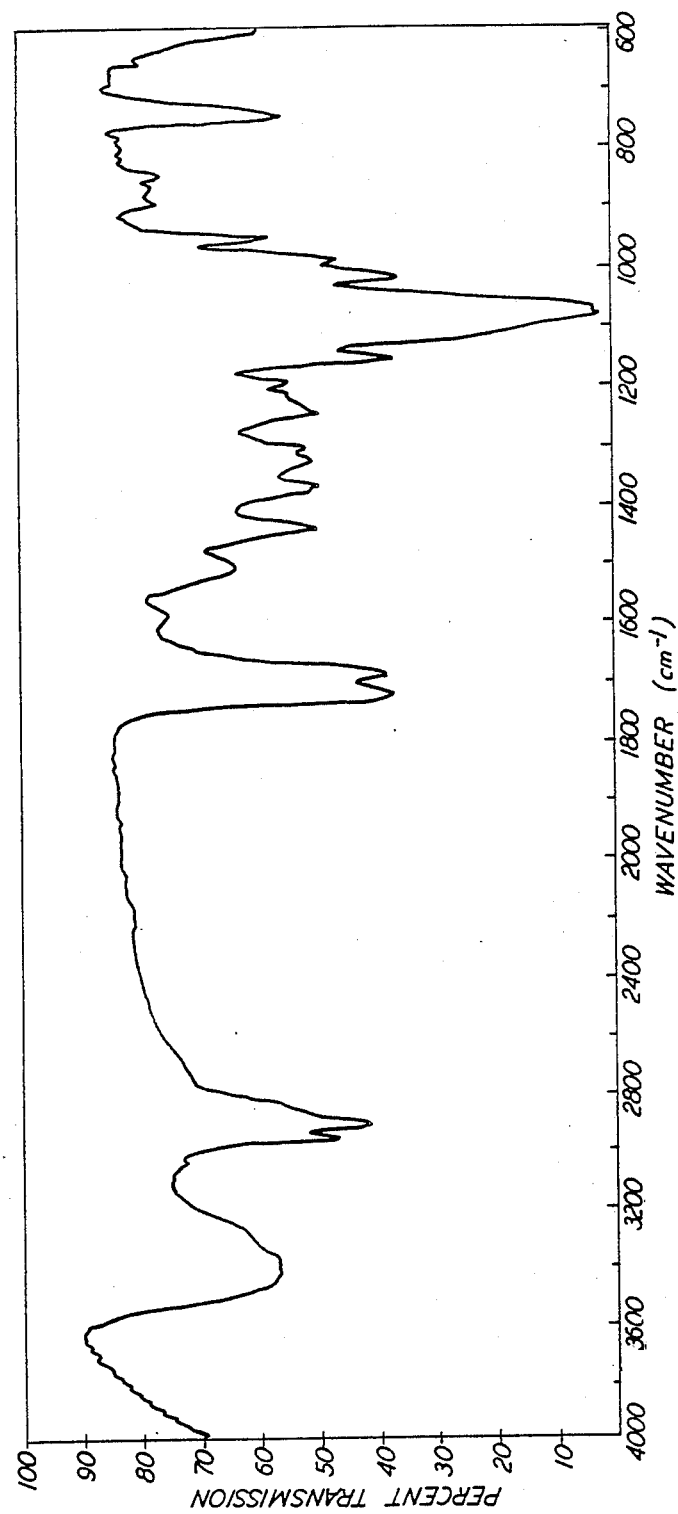
FIG. 3 shows the infrared absorption spectrum of BBM-1675C (KBr, film).
Figure 5:
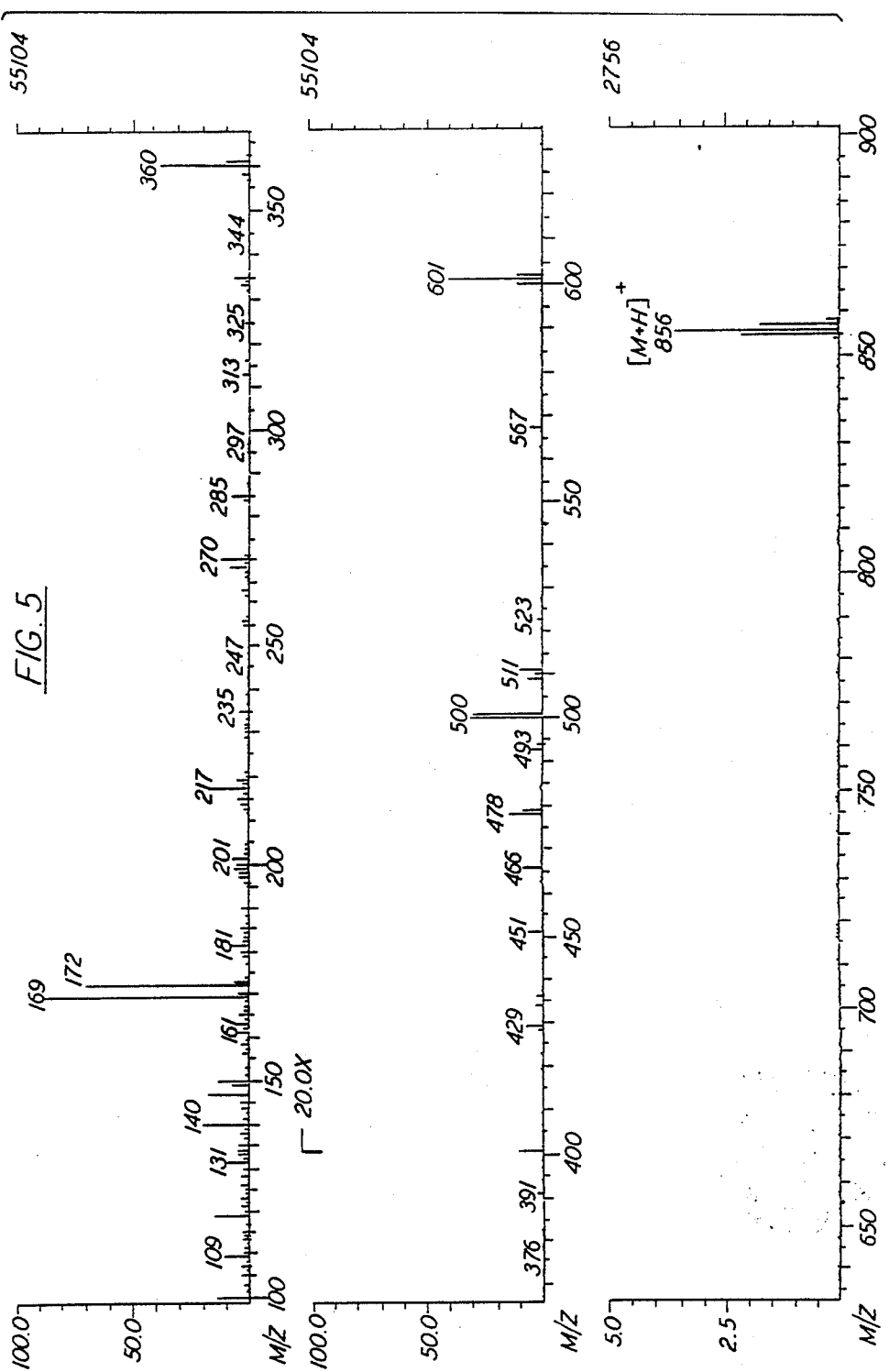
FIG. 5 shows the relative abundance mass spectrum of BBM-1675C.

No significant change is observed with acid or base.
Infrared absorption spectrum: See FIG. 3
Instrument: Nicolet 5DX FT-IR
Major absorption bands (KBr, film):
540, 740, 955, 990, 1017, 1065, 1080, 1118, 1150, 1250, 1305, 1325, 1340, 1370, 1385, 1440, 1690, 1705, 1735, 2900, 2920, 2930, 2970, 3450 cm$^{-1}$.
Mass spectrum: See FIG. 5
Instrument: Finigan 4500 TSQ
Method: fast atom bombardment (FAB) ionization

| Matrix | m/z | Molecular Ion | Relative Abundance |
| --- | --- | --- | --- |
| glycerol | 856 | $[M + H]^+$ | 100% |
| glycerol + NaCl | 878 | $[M + Na]^+$ | 100% |
| dithiothreitol:dithioerythritol (3:1) (w:w) | 856 | $[M + H]^+$ | 100% |

Figure 7:
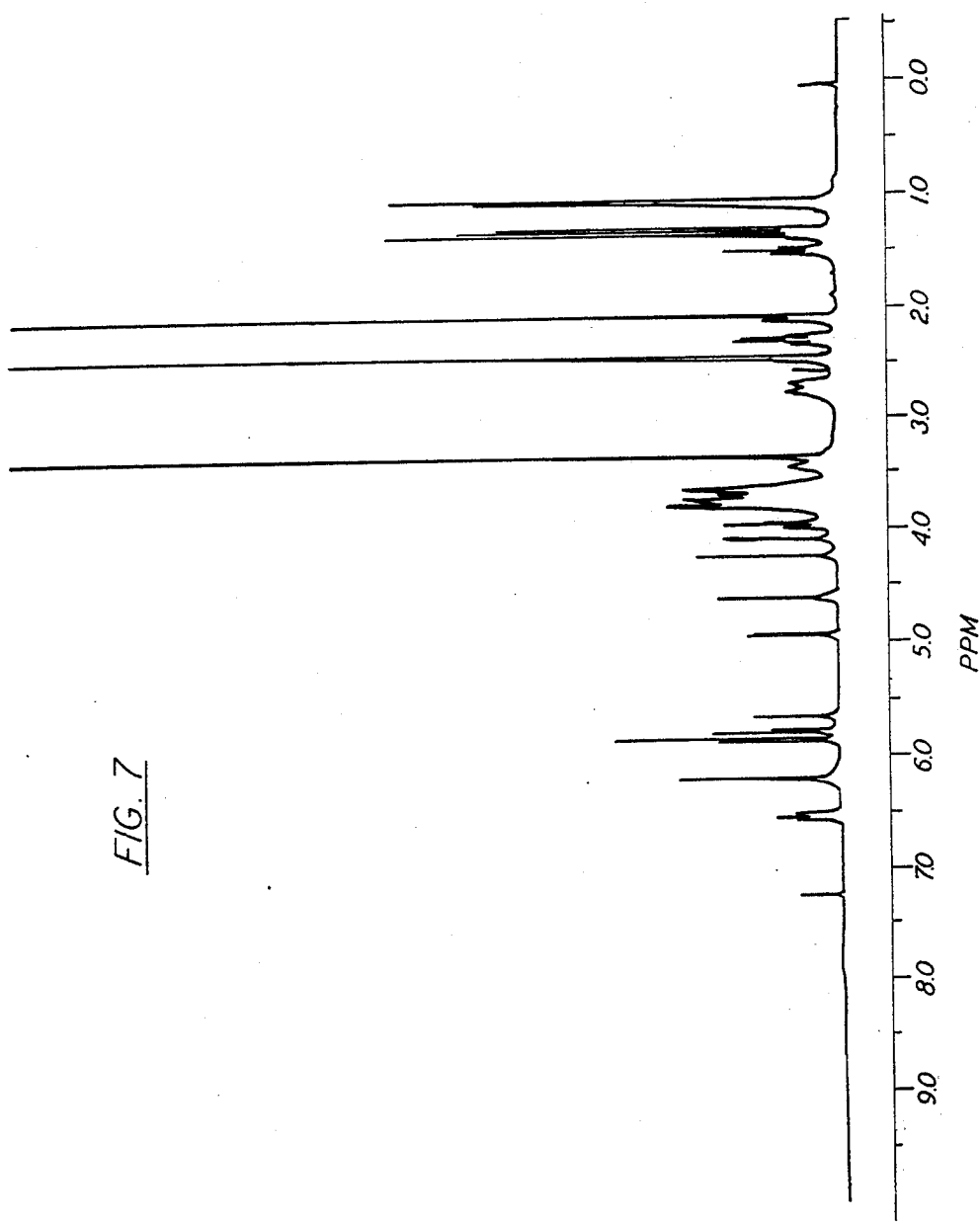
FIG. 7 shows the proton magnetic resonance spectrum of BBM-1675C in $CDCl_3$ (360 MHz).
Figure 9:
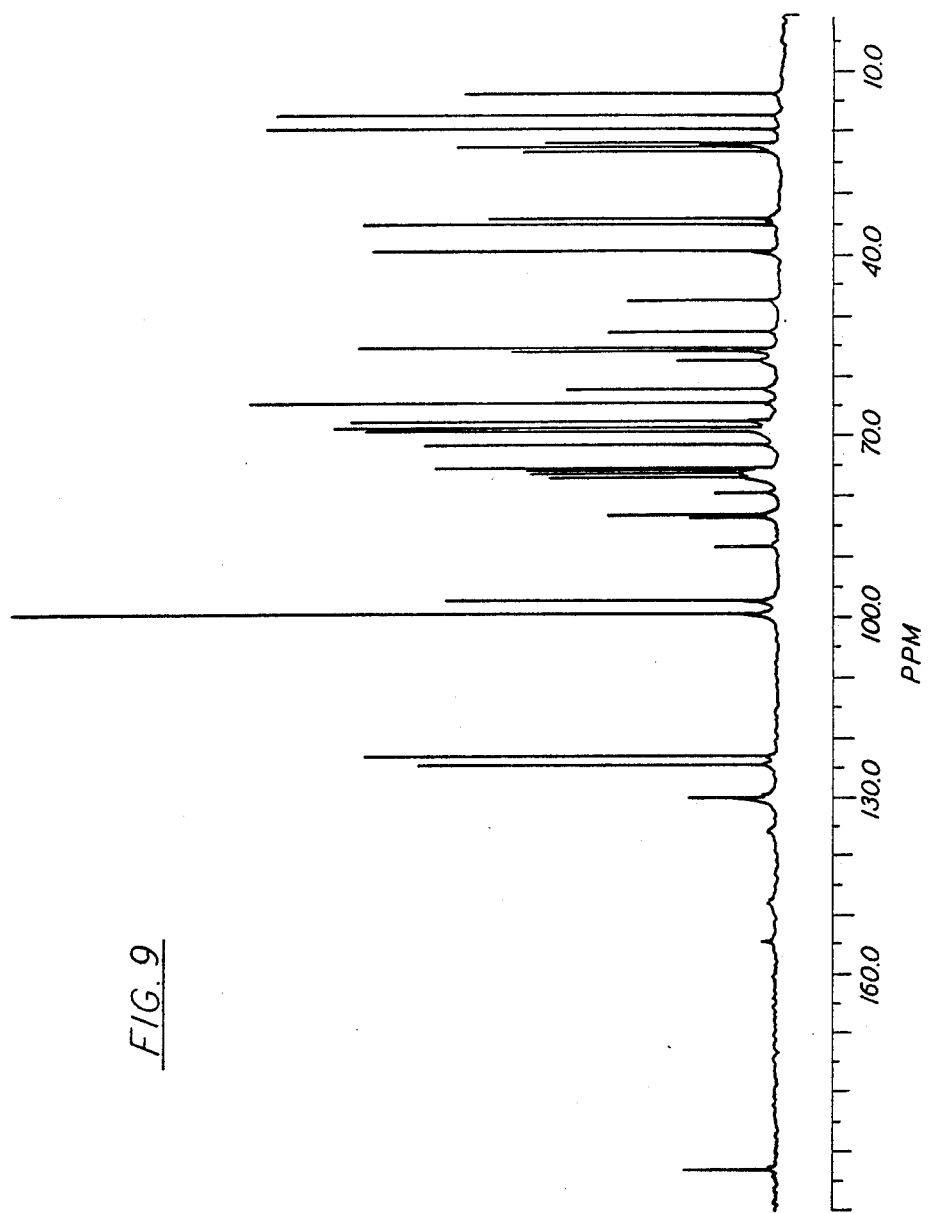
FIG. 9 shows the $^{13}C$ magnetic resonance spectrum of BBM-1675C in $CDCl_3$ (90.6 MHz).

Instrument: Kratos MS-50
High resolution FAB (m/z): $[M + H]^+ = 856.3362$
Molecular weight: apparent MW = 855
(based on above-described mass spectral data)
Elemental composition: $C_{36}H_{61}N_3O_{14}S_3$
(based on above-described high resolution data)
Proton Magnetic Resonance Spectrum: See FIG. 7
Instrument: WM 360 Bruker
Solvent: $CDCl_3$
$^1$H NMR 360 MHz δ (ppm):
6.54 (1H, dd, J = 7.7, 7.0); 6.21 (1H, brs); 5.87 (1H, d, J = 9.6); 5.78 (1H, dd, J = 9.6, 1.5); 5.66 (1H, brd, J = 2.9); 4.94 (1H, dd, J = 10.3, 1.8); 4.61 (1H, d, J = 7.7); 4.25 (1H, s); 4.09 (1H, q, J = 2.6); 3.97 (1H, t, J = 9.6); 3.92–3.53 (10H), 3.45 (1H, dt, J = 10.3, 4.0); 3.37 (3H, s); 2.77 (1H, m); 2.69 (1H, dt, J = 9.9, 5.2); 2.49 (1H, dd, J = 10.3, 2.6); 2.48 (3H, s); 2.30 (2H, m); 2.13 (1H, m); 2.09 (3H, s); 1.50 (2H, m); 1.37 (3H, d, J = 5.9); 1.32 (3H, d, J = 6.3); 1.08 (6H).
C Magnetic Resonance Spectrum: See FIG. 9
Instrument: WM 360 Bruker
Solvent: $CDCl_3$
$^{13}$C NMR 90.6 MHz δ (ppm):
13.7, 17.5, 19.8, 22.3, 22.7, 23.5, 34.2, 35.2, 39.5, 47.7, 52.7, 55.8, 56.1, 57.7, 62.4, 64.7, 67.4, 69.3, 69.8, 71.9, 76.1, 77.1, 77.7, 79.7, 83.2, 88.4, 97.3, -continued
99.7, 123.4, 124.6, 130.1, 193.1.

PHYSICO-CHEMICAL PROPERTIES OF BBM-1675D

Description: amorphous solid
Ultraviolet absorption spectrum: See FIG. 2
Instrument: Hewlett-Packard 8458
Solvent: methanol
Concentration: 0.01 g/l

| $\lambda_{max}$ (nm) | absorptivities |
| --- | --- |
| 214 | 27,000 |
| 274 | 12,800 |
| 325 | 5,400 |

Figure 10B:
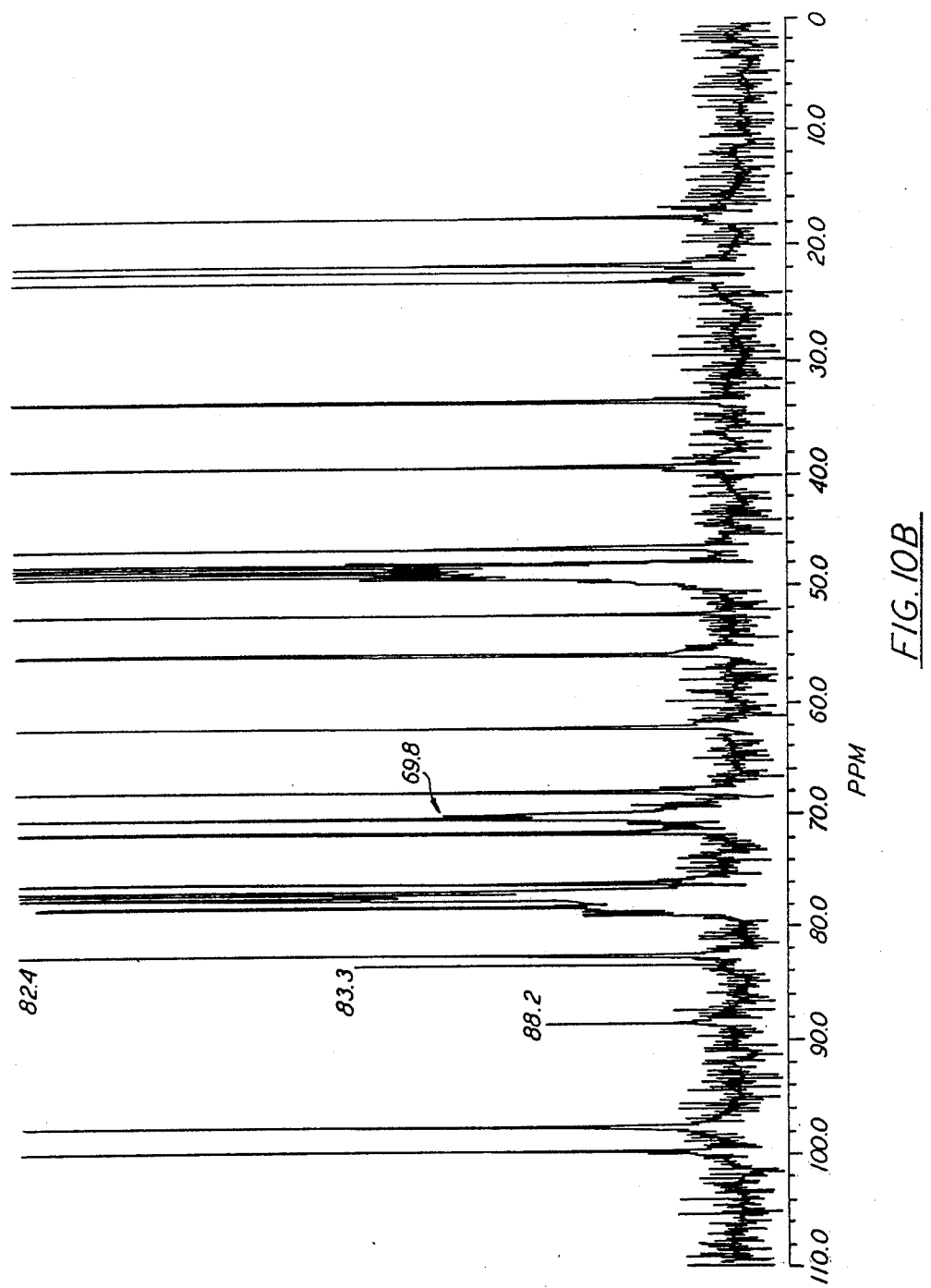
FIG. 10B shows the $^{13}C$ magnetic resonance spectrum (0-110 ppm) of BBM-1675D in $CDCl_3$+10% $CD_3OD$ (90.6 MHz).

No significant change is observed with acid or base.
Infrared absorption spectrum: See FIG. 4
Instrument: Nicolet 5DX FT-IR
Major absorption bands (KBr, film):
735, 755, 910, 960, 1000, 1020, 1085, 1150, 1195, 1250, 1310, 1335, 1365, 1385, 1445, 1510, 1685, 1720, 1735, 2880, 2930, 2960, 3400 cm$^{-1}$.
Mass spectrum: See FIG. 6
Instrument: Finigan 4500 TSQ
Method: fast atom bombardment (FAB) ionization
Matrix: thioglycerol
Molecular ion (m/z): $[M + H]^+ = 696$
Relative abundance: 100%
Instrument: Kratos MS-50
High resolution FAB (m/z): $[M + H]^+ = 696.2794$
Molecular weight: apparent MW = 695
(based on above-described mass spectral data)
Elemental composition: $C_{29}H_{49}N_3O_{12}S_2$
(based on above-described high resolution data)
Correlation of $[M + H]^+$ and $[(M + H) + 2]^+$ relative abundances to their calculated values confirms the elemental composition derived from high resolution-FAB measurements.
Proton magnetic resonance spectrum: See FIG. 8
Instrument: WM 360 Bruker
Solvent: $CDCl_3 + 10\% CD_3OD$
$^1$H NMR 360 MHz δ (ppm):
6.43 (1H, dd, J = 4.4, 10.3); 6.13 (1H, s); 5.81 (1H, d, J = 8.8); 5.70 (1H, d, J = 8.8); 5.48 (1H, 6 brs); 4.48 (1H, d, J = 8.1); 4.02 (1H, d, J = 2.0); 3.95–3.80 (solvent background); 3.77 (1H, t, J = 9.0); 3.70–3.40 (11H, brm); 3.35 (1H, m); 3.28 (3H, s); 3.22 (3H, brs); 2.66–2.55 (2H, m); 2.38 (3H, s); 2.23–2.12 (2H, m); 1.42 (1H, brdt); 1.22 (3H, d, J = 5.9); 0.94 (3H, d, J = 6.6); 0.87 (3H, d, J = 5.9).
$^{13}$C Magnetic resonance spectrum: See FIG. 10A and 10B
Instrument: WM 360 Bruker
Solvent: $CDCl_3 + 10\% CD_3OD$
$^{13}$C NMR 90.6 MHz δ (ppm):
17.5, 21.6, 22.2, 23.0, 33.4, 39.2, 46.4, 52.3, 55.8, 62.1, 67.8, 69.8, 70.1, 71.3, 75.8, 77.1, 78.1, 82.4, 83.3, 88.2, 97.4, 99.6, 122.6, 124.8, 130.1, 130.8, 134.3, 148.7, 192.8.

BIOLOGICAL PROPERTIES OF BBM-1675 SUBSTANCES

Antimicrobial activity of the BBM-1675 substances was determined for a variety of gram-positive and gram-negative microorganisms. Table 1 below provides data in the form of results of an antimicrobial screening procedure involving the parent BBM-1675$A_1$ component and the BBM-1675C and BBM-1675D substances of the present invention. In the screening procedure, each test compound at a uniform concentration of 10 μg/ml of solution impregnated on a paper strip was placed on the growth culture, and the measure of antibiotic activity is the resulting zone of inhibition from the paper strip. As shown in Table 1, the BBM-1675C and D substances showed a broad spectrum of antimicrobial activity which were at least as effective as the BBM-1675A$_1$ component; and in particular, the BBM-1675C and D substances were more effective as inhibitors of gram-negative organisms.

TABLE I

ANTIMICROBIAL ACTIVITY OF BBM-1675 SUBSTANCES

| Test Microorganism | Zone of Inhibition, mm | | |
|---|---|---|---|
| | BBM-1675A$_1$ | BBM-1675C | BBM-1675D |
| *Escherichia coli* AS 19 | 22 | 52 | 51 |
| *Escherichia coli* K 12 | 13 | 36 | 35 |
| *Escherichia coli* P 1373 | 12 | 34 | 33 |
| *Escherichia coli* R Azaserine | 14 | 35 | 34 |
| *Escherichia coli* R Netropsin | 11 | 32 | 32 |
| *Escherichia coli* R Mitomycin C | 12 | 35 | 34 |
| *Escherichia coli* R Bleomycin | 16 | 38 | 36 |
| *Escherichia coli* R Daunomycin | 19 | 45 | 44 |
| *Escherichia coli* R Neomycin | 24 | 53 | 52 |
| *Escherichia coli* R Sibiromycin | 14 | 32 | 30 |
| *Escherichia coli* R Hedamycin | 14 | 30 | 25 |
| *Escherichia coli* R Aclacinomycin | 15 | 41 | 40 |
| *Bacillus subtilis* ATCC 6633 | 34 | 43 | 41 |
| *Klebsiella pneumoniae* | 17 | 35 | 35 |
| *Staphylococcus* 209 P | 32 | 47 | 44 |
| *Staphylococcus* R Actinoleukin | 33 | 35 | 33 |
| *Staphylococcus* R Streptonigrin | 37 | 50 | 48 |
| *Staphylococcus faecalis* P1377 | 30 | 39 | 38 |
| *Streptococcus aureus* Smith P | 36 | 47 | 45 |
| *Staphylococcus aureus* Smith R Actinomycin D | 40 | 55 | 53 |
| *Staphylococcus aureus* Smith R Aureolic acid | 17 | 32 | 31 |
| *Acinetobacter* | 16 | 33 | 32 |
| *Micrococcus luteus* | 35 | 57 | 55 |
| *Saccharomyces cerevisiae* petite | 22 | 42 | 43 |

R = resistant to named antibiotic

ACTIVITY AGAINST P-388 LEUKEMIA

Tables II and III contain the results of laboratory tests with CDF$_1$ mice implanted intraperitoneally with a tumor inoculum of 10$^6$ ascites cells of P-388 leukemia and treated with various doses of BBM-1675A$_1$, C or D. The substances were administered by intraperitoneal injection. Groups of six mice were used for each dosage amount, and they were treated with a single dose of the substance on the day after inoculation. A group of ten saline treated control mice was included in each series of experiments. The BBM-1675A$_1$ treated group in Table III was included as a direct comparison. A 30-day protocol was employed with the mean survival time in days being determined for each group of mice and the number of survivors at the end of the 5-day period being noted. The mice were weighed before treatment and again on day four. The change in weight was taken as a measure of drug toxicity. Mice weighing 20 grams each were employed, and a loss in weight of up to approximately 2 grams was not considered excessive. The vehicle treated control animals usually died within nine days. The results were determined in terms of a T/C which is the ratio of the mean survival time of the treated group to the mean survival time of the vehicle treated control group times 100. An effect in terms of % T/C equal to or greater than 125 indicates that a significant antitumor effect was achieved. The screening results in Table II show the initially unexpected level of antitumor activity of the BBM-1675C substance. In Table III, the results of a direct comparison of BBM-1675A$_1$ (esperamicin A$_1$) and the BBM-1675C and BBM-1675D substances are reported. The data suggest that BBM-1675C is about comparable to BBM-1675A$_1$ in potency and antitumor effectiveness and that it is not schedule dependent, while BBM-1675D is only slightly less effective.

Additionally, it is reported in the present invention that the same substances BBM-1675C and BBM-1675D can also be obtained from the BBM-1675A$_2$ (esperamicin A$_2$) component. In comparison of the data reported herein for BBM-1675C and BBM-1675D and the data reported in published U.K. Patent Application No. 2,141,425 for the BBM-1675A$_2$ component, it is surprisingly found that the substances BBM-1675C and D are more effective as antitumor agents than the parent BBM-1675A$_2$ component from which they were derived.

TABLE II

EFFECT OF BBM-1675C ON P-388 LEUKEMIA (Day 1 Treatment)

| Compound | Dose, IP mg/kg/inj. | MST days | Effect MST % T/C | AWC gm Day 4 | Survivors Day 5 |
|---|---|---|---|---|---|
| BBM-1675C | 3.2 | TOX | TOX | — | 0/6 |
| | 0.8 | TOX | TOX | — | 0/6 |
| | 0.2 | TOX | TOX | — | 0/6 |
| | 0.05 | TOX | TOX | −1.8 | 1/6 |
| | 0.0125 | 11.0 | 122 | −2.5 | 5/6 |
| | 0.003125 | 13.5 | 150 | −2.5 | 6/6 |
| Vehicle | — | 9.0 | 100 | 0.4 | 10/10 |

Tumor inoculum: 10$^6$ ascites cells implanted i.p.
Host: CDF$_1$ male mice
Evaluation: MST = median survival time
Effect: % T/C = (MST treated/MST control) × 100
Criteria: % T/C ≥ 125 considered significant antitumor activity
AWC: average weight change (treated-control) in grams (on day 4)

TABLE III

EFFECT OF BBM-1675 SUBSTANCES ON P-388 LEUKEMIA

| Compound | Treatment Schedule | Dose, IP mg/kg/inj. | MST days | Effect MST % T/C | AWC gm Day 4 | Survivors Day 5 |
|---|---|---|---|---|---|---|
| BBM-1675A$_1$ | d. 1 | 0.0512 | TOX | TOX | — | 0/6 |
| | | 0.0256 | TOX | TOX | — | 0/6 |
| | | 0.0128 | TOX | TOX | −1.8 | 3/6 |

TABLE III-continued
EFFECT OF BBM-1675 SUBSTANCES ON P-388 LEUKEMIA

| Compound | Treatment Schedule | Dose, IP mg/kg/inj. | MST days | Effect MST % T/C | AWC gm Day 4 | Survivors Day 5 |
|---|---|---|---|---|---|---|
| | | 0.0064 | 15.5 | 172 | −0.3 | 6/6 |
| | | 0.0032 | 15.0 | 167 | −0.6 | 6/6 |
| | | 0.0016 | 15.5 | 172 | 0.6 | 6/6 |
| | | 0.0008 | 12.5 | 139 | 0.3 | 6/6 |
| | | 0.0004 | 12.0 | 133 | 1.4 | 6/6 |
| | | 0.0002 | 11.0 | 122 | 0.8 | 6/6 |
| | | 0.0001 | 11.5 | 128 | 1.4 | 6/6 |
| BBM-1675C | d. 1 | 0.0256 | TOX | TOX | — | 0/6 |
| | | 0.0128 | TOX | TOX | −0.8 | 3/6 |
| | | 0.0064 | 11.5 | 128 | −0.3 | 6/6 |
| | | 0.0032 | 14.5 | 161 | −0.1 | 6/6 |
| | | 0.0016 | 10.5 | 117 | 0.0 | 6/6 |
| | | 0.0008 | 12.0 | 133 | 0.3 | 6/6 |
| | | 0.0004 | 11.5 | 128 | 0.8 | 6/6 |
| | | 0.0002 | 11.0 | 122 | 1.4 | 6/6 |
| | | 0.0001 | 11.0 | 122 | 0.8 | 6/6 |
| | | 0.00005 | 10.5 | 117 | 1.3 | 6/6 |
| BBM-1675D | d. 1 | 0.0256 | 9.0 | 100 | 0.1 | 6/6 |
| | | 0.0128 | 11.5 | 128 | 0.3 | 6/6 |
| | | 0.0064 | 12.5 | 139 | 0.3 | 6/6 |
| | | 0.0032 | 12.0 | 133 | 0.1 | 6/6 |
| | | 0.0016 | 11.5 | 128 | 0.8 | 6/6 |
| | | 0.0008 | 10.0 | 111 | 0.2 | 6/6 |
| | | 0.0004 | 10.0 | 111 | 0.5 | 6/6 |
| | | 0.0002 | 9.5 | 106 | 1.7 | 6/6 |
| | | 0.0001 | 9.5 | 106 | 1.7 | 6/6 |
| | | 0.00005 | 9.0 | 100 | 2.0 | 6/6 |
| BBM-1675C | d. 1→5 | 0.0032 | 16.0 | 178 | −1.3 | 6/6 |
| | | 0.0016 | 13.5 | 150 | −1.0 | 6/6 |
| | | 0.0008 | 13.5 | 150 | −0.3 | 6/6 |
| | | 0.0004 | 12.0 | 133 | −0.4 | 6/6 |
| | | 0.0002 | 12.0 | 133 | −0.4 | 6/6 |
| | | 0.0001 | 11.0 | 122 | −0.4 | 5/6 |
| | | 0.00005 | 11.0 | 122 | 0.9 | 6/6 |
| | | 0.000025 | 8.5 | 94 | 2.2 | 6/6 |
| | | 0.0000125 | 8.0 | 89 | 2.4 | 6/6 |
| | | 0.00000625 | 8.0 | 89 | 2.4 | 6/6 |
| Vehicle | | — | 9.0 | 100 | 2.4 | 10/10 |

Tumor inoculum: $10^6$ ascites cells implanted i.p.
Host: $CDF_1$ female mice
Evaluation: MST = median survival time
Effect: % T/C = (MST treated/MST control) × 100
Criteria: % T/C ≧ 125 considered significant antitumor activity
AWC: average weight change (treated-control) in grams (on day 4)

ACTIVITY AGAINST B16 MELANOMA

Table IV contains results of antitumor tests using the B16 melanoma grown in mice. $BDF_1$ mice were employed and inoculated subcutaneously with the tumor implant. A 60-day protocol was used. Groups of ten mice were used for each dosage amount tested, and the mean survival time for each group was determined. Control animals inoculated in the same way as the test animals and treated with the injection vehicle and no drug exhibited a mean survival time of 22.5 days. For each dosage level, the test animals were treated with the test compound on days 1, 5 and 9 by intraperitoneal injection. An effect in terms of % T/C equal to or greater than 125 indicates that a significant antitumor effect was achieved. The results in Table IV show that in a direct comparison BBM-1675C was also effective in treatment of mice bearing B16 melanoma and was about comparable to $BBM-1675A_1$ in potency.

TABLE IV
EFFECT OF BBM-1675 SUBSTANCES ON B16 MELANOMA
(Day 1, 5 and 9 Treatments)

| Compound | Dose, IP mg/kn/inj. | MST days | Effect MST % T/C | AWC gm Day 12 | Survivors Day 10 |
|---|---|---|---|---|---|
| $BBM-1675A_1$ | 0.0032 | 37.5 | 167 | 0.3 | 10/10 |
| | 0.0016 | 37.5 | 167 | 0.3 | 10/10 |
| | 0.0008 | 38.5 | 171 | 1.4 | 10/10 |
| | 0.0004 | 37.0 | 164 | 1.8 | 10/10 |
| | 0.0002 | 34.5 | 153 | 2.0 | 10/10 |
| | 0.0001 | 32.0 | 142 | 1.9 | 10/10 |
| BBM-1675C | 0.0008 | 31.5 | 140 | 0.6 | 10/10 |
| | 0.0004 | 37.0 | 164 | 1.2 | 10/10 |
| | 0.0002 | 31.0 | 138 | 0.6 | 10/10 |
| | 0.0001 | 31.5 | 140 | 1.0 | 10/10 |
| | 0.00005 | 27.5 | 122 | 0.8 | 10/10 |
| | 0.000025 | 25.0 | 111 | 0.5 | 10/10 |
| Vehicle | — | 22.5 | 100 | 0.3 | 10/10 |

Tumor inoculum: 0.5 ml of a 10% brei, IP
Host: $BDF_1$ female mice
Evaluation: MST = median survival time
Effect: % T/C = (MST treated/MST control) × 100
Criteria: % T/C ≧ 125 considered significant antitumor activity
AWC: average weight change (treated-control) in grams (on day 12)

As indicated by the antimicrobial and mouse tumor data provided above, BBM-1675C and BBM-1675D are thus useful as antibiotics in the therapeutic treatment of mammals and other animals for infectious diseases and also as antitumor agents for therapeutically inhibiting the growth of mammalian tumors.

The present invention, therefore, provides a method for therapeutically treating an animal host affected by a microbial infection or by a malignant tumor which comprises administering to said host an effective antimicrobial or tumor-inhibiting dose of BBM-1675C or BBM-1675D, or a pharmaceutical composition thereof.

The invention includes within its scope pharmaceutical compositions containing an effective antimicrobial or tumor-inhibiting amount of BBM-1675C or BBM-1675D in combination with an inert pharmaceutically acceptable carrier or diluent. Such compositions may also contain other active antimicrobial or antitumor agents and may be made up in any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile aqueous or non-aqueous solutions, suspensions or emulsions. They may also be manufactured in the form of sterile solid compositions which can be dissolved in sterile water, physiological saline or some other sterile injectable medium immediately before use.

For use as an antimicrobial agent, the BBM-1675C or BBM-1675D, or a pharmaceutical composition thereof is administered so that the concentration of active ingredient is greater than the minimum inhibitory concentration for the particular organism being treated. For use as an antitumor agent, optimal dosages and regimens of BBM-1675C or BBM-1675D for a given mammalian host can be readily ascertained by those skilled in the art. It will, of course, be appreciated that the actual dose of BBM-1675C or BBM-1675D used will vary according to the particular composition formulated, the mode of application and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease. Administration can be carried out continuously or periodically within the maximum tolerated dose. Optimal application rates for a given set of conditions can be ascertained by those skilled in the art using conventional dosage determination tests in view of the above guidelines.

The following examples are provided for illustrative purposes only and are not intended to limit the scope of the invention.

CHEMICAL PREPARATION AND ISOLATION OF BBM-1675C and BBM-1675D

Example 1

A sample of BBM-1675A$_1$ (50 mg) was dissolved in 2.5 ml of methanol and treated with 2.5 ml of 0.1 molar solution of hydrogen chloride in methanol. The reaction was allowed to proceed at a temperature of about 50° C, and the disappearance of the starting material (approximately 30 minutes) was monitored every 5 to 10 minutes by thin layer chromatography (TLC) on silica gel plates (Analtech, 250 micron, GF) with toluene:acetone (3:2, v/v) as the eluting solvent After the starting material has been consumed, the reaction mixture was neutralized with a saturated solution of NaHCO$_3$ in methanol, then evaporated under reduced pressure to yield a dry residue containing the bioactive fragments. The BBM-1675C substance was isolated from the residue by flash column chromatography on a 2 cm i.d. × 10 cm column packed with Woelm silica gel (32-63 micron particle size). The column was eluted with toluene:acetone (3:2, v/v) collecting 3 ml fractions. Each fraction was analyzed by TLC [silica gel with toluene:acetone (3:2, v/v) as eluent], and the TLC spots were visualized with a UV 254 nm light source and a ceric sulfate spray (1% ceric sulfate and 2.5% molybolic acid in 10% sulfuric acid). Fractions 6-12 (R$_f$ value for BBM-1675C is 0.28) were pooled and evaporated to dryness to yield 12 mg (35%) of substantially pure BBM-1675C.

The physico-chemical properties of BBM-1675C appear in the specification and the ultraviolet, infrared, mass, $^1$H NMR and $^{13}$C NMR spectra of the compound appear as FIGS. 1, 3, 5, 7 and 9, respectively.

Example 2

When the reaction time of the procedure in Example 1 is extended, the amount of BBM-1675C decreases, and two new products denoted as compound 3 (R$_f$=0.65) and BBM-1675D (R$_f$ remains at baseline) [TLC: silica, toluene:acetone (3:2, v/v)] appear and become more prominent with time.

Compound BBM-1675D which usually accompanies the production of BBM-1675C was isolated from the chromatographic column described in Example 1 by eluting the column with chloroform:methanol (5:1, v/v). The appropriate fractions were pooled and evaporated to dryness to yield 18 mg of substantially pure BBM-1675D from the reaction described in Example 1.

The BBM-1675D substance exhibits one major spot at R$_f$=0.37 in reverse phase TLC (Whatman MKC$_{18}$F, 200 micron) using 30% water in methanol as the eluent and R$_f$=0.22 in normal phase silica gel TLC using chloroform:methanol (5:0.5, v/v) as the eluent.

Example 3

Substantial improvement in the yield of BBM-1675D can be achieved by using p-toluenesulfonic acid in place of hydrogen chloride in the chemical hydrolysis of BBM-1675A$_2$ or BBM-1675A$_1$ as illustrated by the procedures of Examples 3 and 5, respectively.

A sample of BBM-1675A$_2$ (15.2 mg) was hydrolyzed with 0.03 molar solution of p-toluenesulfonic acid in methanol (1 ml) at a temperature of about 63° C. for about one hour. The reaction mixture was then evaporated to dryness under reduced pressure at about 30° C. The BBM-1675D substance was isolated from the dry residue by flash column chromatography on a column packed with Woelm silica gel (32-63 micron particle size). The column was eluted with chloroform:methanol (5:0.5, v/v), and the collected fractions were analyzed by TLC [silica gel with chloroform:methanol (5:0.5, v/v) as eluent]. The applied chromatography conditions permitted the separation of the mixture of inactive compounds 2 and 3 (7 mg) from the bioactive BBM-1675D substance which has an R$_f$ value of 0.22. The appropriate fractions were pooled and evaporated to dryness to yield 8 mg of substantially pure BBM-1675D in near quantitative yield.

The physico-chemical properties of BBM-1675D appear in the specification and the ultraviolet, infrared, mass, $^1$H NMR and $^{13}$C NMR spectra of the compound appear as FIGS. 2, 4, 6, 8 and combined 10A and 10B, respectively.

Example 4

A sample of BBM-1675A$_2$ (40 mg) was treated with 5 ml of an 0.5 molar solution of hydrogen chloride in methanol at about 50° C. for about 2 hours according to the general procedure and isolation method described in Example 1. After neutralization with NaHCO$_3$ and evaporation to dryness, the BBM-1675C substance was isolated from the residue by flash column chromatography on a column packed with Woelm silica gel (32–63 micron particle size) using toluene:acetone (3:2, v/v) as the eluent. The appropriate fractions were combined and evaporated to dryness to yield 8.4 mg of substantially pure BBM-1675C which is identical to the product isolated in Example 1.

The chromatographic column of above was then eluted with chloroform:methanol (5:0.25, v/v) and the fractions collected were pooled and evaporated to dryness to yield BBM-1675D. The BBM-1675D substance was further purified by an additional flash chromatography column with silica gel utilizing chloroform:methanol (5:0.5, v/v) as the eluent. The appropriate fractions were combined and evaporated to dryness to yield 6.3 mg of substantially pure BBM-1675D which is identical to the product isolated in Example 3.

Example 5

A sample of BBM-1675A$_1$ (49.3 mg) was hydrolyzed with 0.037 M solution of p-toluenesulfonic acid in methanol (1.5 ml) at a temperature of about 60° C. for about 1.5 hours. The reaction mixture was evaporated to dryness under reduced pressure at about 30° C. to give a residue which contains BBM-1675D and the inactive compounds 1 and 3. The BBM-1675D bioactive substance was isolated from the residue by flash column chromatography on a column packed with Woelm silica gel (32–63 micron particle size) utilizing chloroform:methanol (5:0.25, v/v) as the eluent. The appropriate fractions were combined and evaporated to dryness to yield 27 mg of substantially pure BBM-1675D which is identical to the product isolated in Example 3.

Example 6

A sample of BBM-1675C (5.1 mg) was hydrolyzed with 0.5 molar solution of hydrogen chloride in methanol (1 ml) at about 40–50° C. overnight. After neutralization with NaHCO$_3$ and evaporation to dryness, the BBM-1675D bioactive substance was isolated from the residue by flash column chromatography on a column packed with Woelm silica gel (32–63 micron particle size) utilizing chloroform:methanol (5:0.25, v/v) as the eluent. The appropriate fractions yielded substantially pure BBM-1675D which is identical to the product isolated in Example 3.

Example 7

When the general procedure of Examples 1 and 2 are repeated, except that the starting material BBM-1675A$_1$ is replaced by an equimolar amount of a mixture containing BBM-1675A$_1$ and BBM-1675A$_2$, there is thereby produced the BBM-1675C and BBM-1675D substances.

Example 8

When the general procedure of Example 5 is repeated, except that the starting material BBM-1675A$_1$ is replaced by an equimolar amount of a mixture containing BBM-1675A$_1$ and BBM-1675A$_2$, there is thereby produced the BBM-1675D substance.

Figure 2:
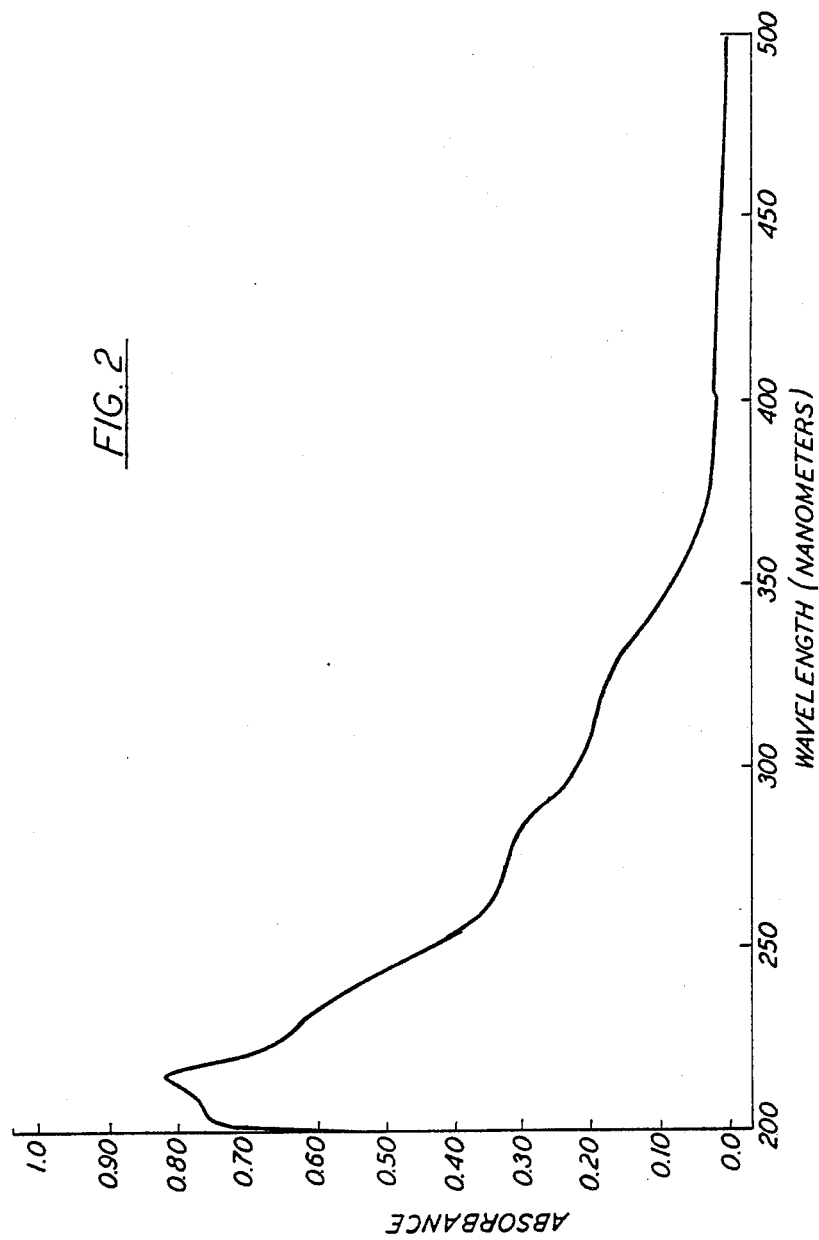
FIG. 2 shows the ultraviolet absorption spectrum of BBM-1675D.
Figure 4:
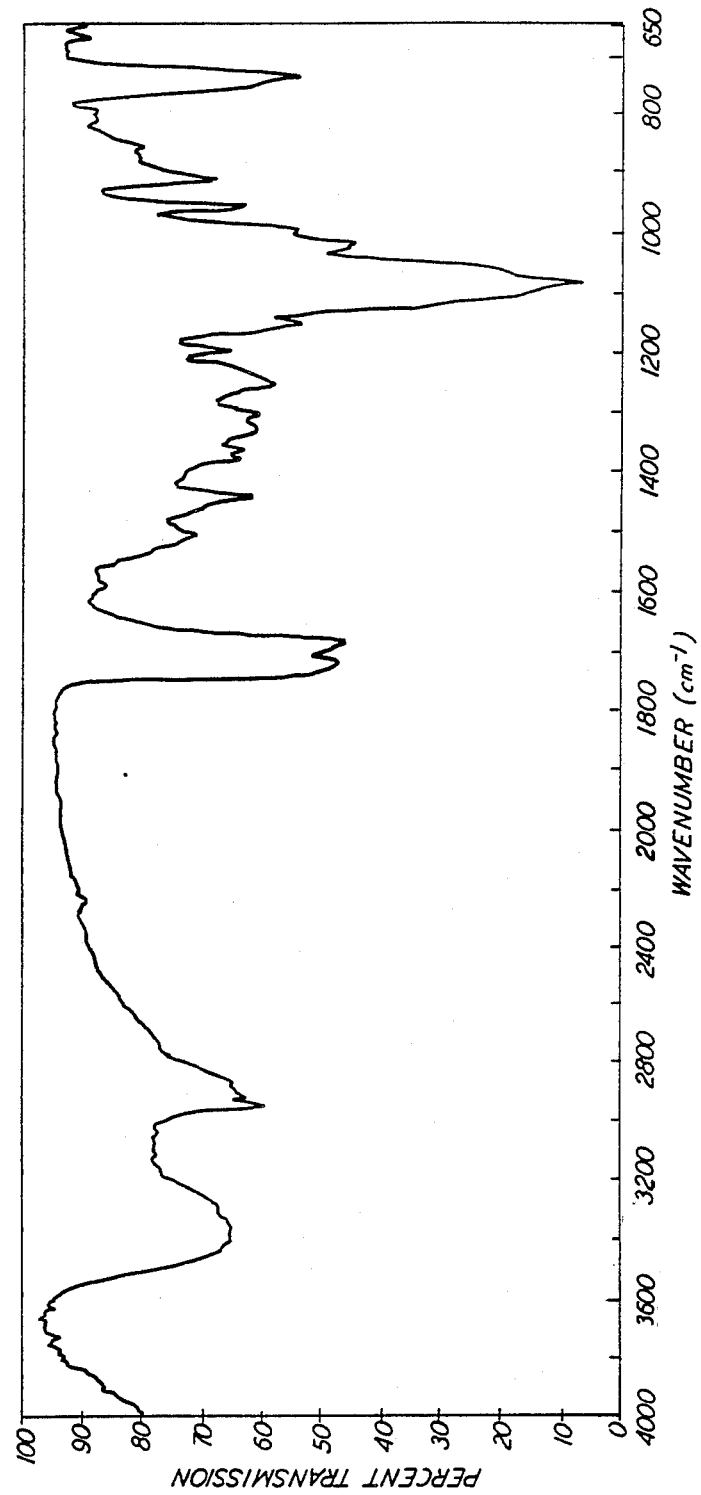
FIG. 4 shows the infrared absorption spectrum of BBM-1675D (KBr, film).
Figure 6:
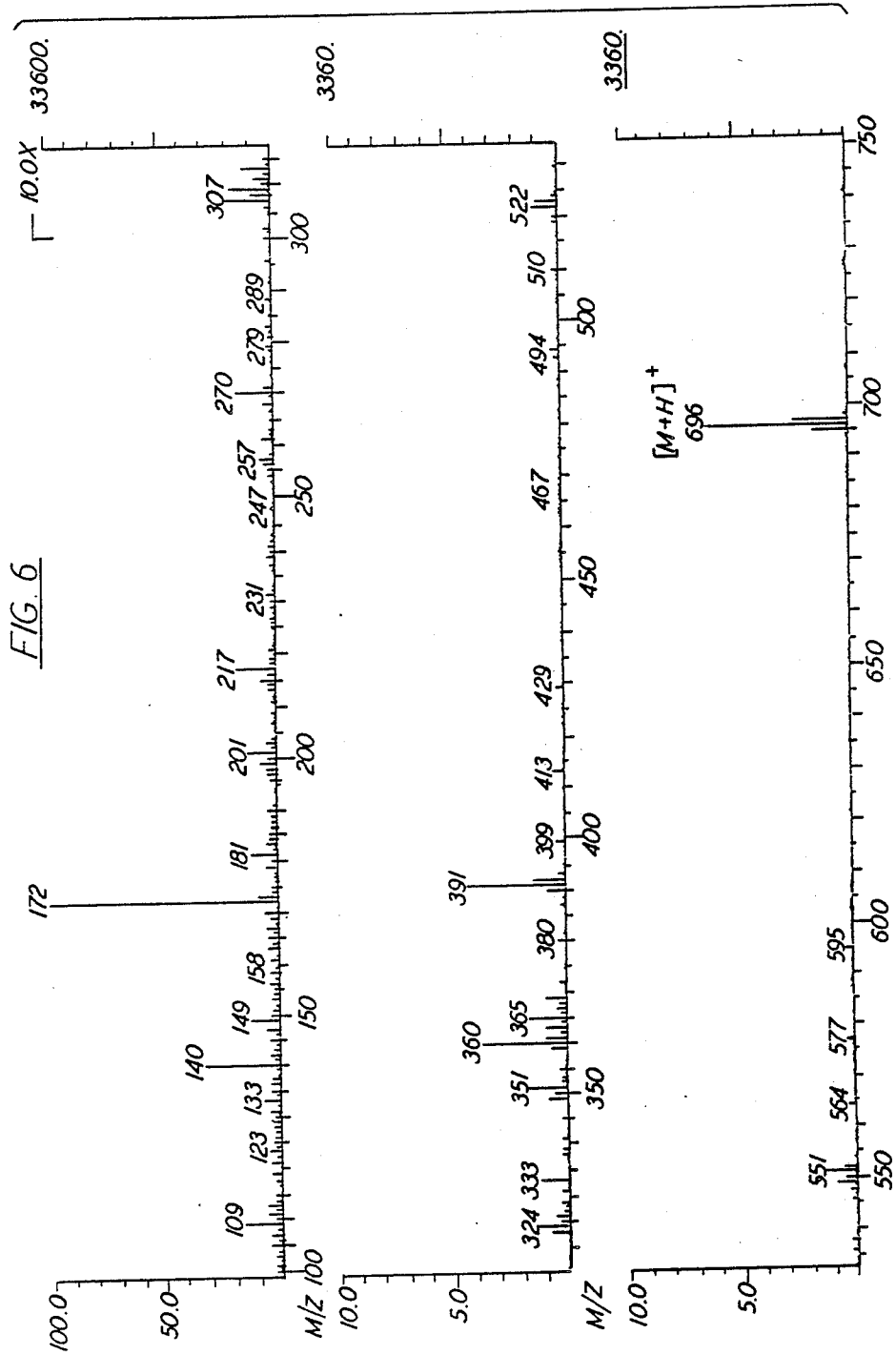
FIG. 6 shows the relative abundance mass spectrum of BBM-1675D.
Figure 8:
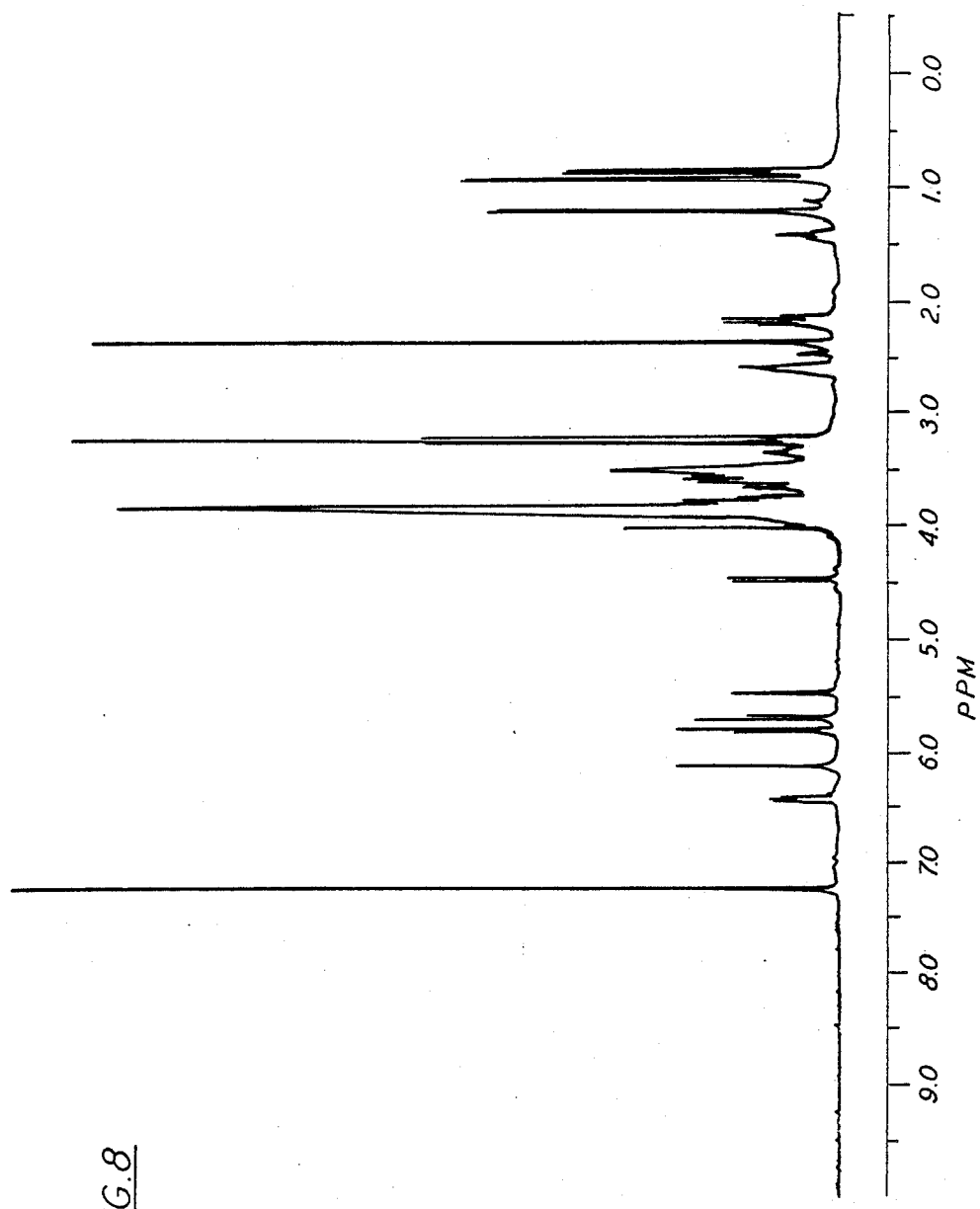
FIG. 8 shows the proton magnetic resonance spectrum of BBM-1675D in $CDCl_3$ +10% CD30D (360 MHz).

I claim:

1. The antitumor antibiotic BBM-1675D which in substantially pure form:
   (a) appears as an amorphous solid;
   (b) is soluble in methanol, ethanol, acetone and tetrahydrofuran, and slightly soluble in chloroform;
   (c) exhibits in silica gel thin-layer chromatography an $R_f$ value of 0.22 with the solvent system chloroform:methanol (5:0.5, v/v) and exhibits in reverse phase silica gel thin layer chromatography an $R_f$ value of 0.37 with the solvent system methanol:water (70:30, v/v);
   (d) has an apparent molecular weight of 695 as determined by high resolution FAB mass spectroscopy;
   (e) has an ultraviolet absorption spectrum in methanol solution substantially as shown in FIG. 2 exhibiting ultraviolet absorption maxima and absorptivities at 214 nm (a=27,000), 274 nm (a=12,800), and 325 nm (a=5,400) with no significant change upon addition of acid or base;
   (f) has an infrared absorption spectrum (KBr, film) substantially as shown in FIG. 4 exhibiting principal absorption peaks at
   735, 755, 910, 960, 1000, 1020, 1085, 1150, 1195, 1250, 1310, 1335, 1365, 1385, 1445, 1510, 1685, 1720, 1735, 2880, 2930, 2960 and 3400 reciprocal centimeters;
   (g) has a low resolution mass spectrum substantially as shown in FIG. 6 exhibiting a molecular ion $[M+H]^+$ of 696;
   (h) has a 360 MHz proton magnetic resonance spectrum in CDCl$_3$+10% CD$_3$OD substantially as shown in FIG. 8 exhibiting signals at 6.43 (1H, dd, J=4.4, 10.3); 6.13 (1H, s); 5.81 (1H, d, J=8.8); 5.70 (1H, d, J=8.8); 5.48 (1H, 6 brs); 4.48 (1H, d, J=8.1); 4.02 (1H, d, J=2.0); 3.95-3.80 (solvent background); 3.77 (1H, t, J=9.0); 3.70-3.40 (11H, brm); 3.35 (1H, m); 3.28 (3H, s); 3.22 (3H, brs); 2.66-2.55 (2H, m); 2.38 (3H, s); 2.23-2.12 (2H, m); 1.42 (1H, brdt); 1.22 (3H, d, J=5.9); 0.94 (3H, d, J=6.6); and 0.87 (3H, d, J=5.9) parts per million downfield from tetramethylsilane;
   (i) has a 90.6 MHz carbon-13 magnetic resonance spectrum in CDCl$_3$+10% CD$_3$OD substantially as shown in FIG. 10 (FIG. 10A+10B) exhibiting signals at 17.5, 21.6, 22.2, 23.0, 33.4, 39.2, 46.4, 52.3, 55.8, 62.1, 67.8, 69.8, 70.1, 71.3, 75.8, 77.1, 78.1, 82.4, 83.3, 88.2, 97.4, 99.6, 122.6, 124.8, 130.1, 130.8, 134.3, 148.7, and 192.8 parts per million downfield from tetramethylsilane.

2. A pharmaceutical composition comprising an effective antimicrobial amount of BBM-1675D in combination with a pharmaceutical carrier or diluent.

3. A pharmaceutical composition comprising an effective tumor-inhibiting amount of BBM-1675D in combination with a pharmaceutical carrier or diluent.

4. A method for therapeutically treating an animal host affected by a microbial infection, which comprises administering to said host an effective antimicrobial dose of BBM-1675D.

* * * * *